United States Patent
Lossau et al.

(10) Patent No.: US 7,301,637 B2
(45) Date of Patent: Nov. 27, 2007

(54) DARK FIELD IMAGING DEVICE FOR THE SPATIALLY-RESOLVED DARK FIELD IMAGING OF A SAMPLE AND EXAMINATION METHOD

(75) Inventors: Harald Lossau, Ehrengutstr. 8, D-80469 München (DE); Christian Musewald, Töging am Inn (DE)

(73) Assignee: Harald Lossau, Munich (DE)

( * ) Notice: Subject to any disclaimer, the term of this patent is extended or adjusted under 35 U.S.C. 154(b) by 319 days.

(21) Appl. No.: 10/495,318

(22) PCT Filed: Nov. 8, 2002

(86) PCT No.: PCT/DE02/04145

§ 371 (c)(1),
(2), (4) Date: Oct. 8, 2004

(87) PCT Pub. No.: WO03/042671

PCT Pub. Date: May 22, 2003

(65) Prior Publication Data
US 2005/0041245 A1    Feb. 24, 2005

(30) Foreign Application Priority Data
Nov. 12, 2001   (DE)  ............................... 101 55 142

(51) Int. Cl.
*G01N 21/25*   (2006.01)
*G01N 21/00*   (2006.01)
*G01J 3/30*    (2006.01)

(52) U.S. Cl. ...................... 356/417; 356/338; 356/317; 356/340; 356/420

(58) Field of Classification Search ........ 356/317–318, 356/416, 417, 420, 338, 340; 250/458.1–461.2
See application file for complete search history.

(56) References Cited

U.S. PATENT DOCUMENTS 4,734,578 A * 3/1988 Horikawa ................... 250/234
5,028,802 A * 7/1991 Webb et al. ................ 250/235

(Continued)

FOREIGN PATENT DOCUMENTS

DE         28 52 203 B2    7/1981

(Continued)

*Primary Examiner*—Gregory J. Toatley, Jr.
*Assistant Examiner*—Bryan J Giglio
(74) *Attorney, Agent, or Firm*—Thelen Reid Brown Raysman & Steiner

(57) ABSTRACT

Described is a dark-field imaging device for the spatially resolved dark-field imaging of a sample (60), especially a fluorescent sample, comprising, for the illumination of the sample with excitation light, an illumination assembly (20) comprising a grid (22) of individually addressable light sources (24), wherein the lines connecting the light sources and the sample define a region (64) with the optical path of the direct excitation light and a region (66) with the optical path of the specular reflected excitation light, and a detection assembly (30) for the detection, with radiation-receiving elements (34), of the radiation emitted by the sample (60) as an optical response to the illumination, wherein the radiation-receiving elements (34) of the detection assembly (30) are disposed outside the region (64) with the optical path of the direct excitation light and the region (66) with the optical path of the specular reflected excitation light.

20 Claims, 2 Drawing Sheets

U.S. PATENT DOCUMENTS

| | | | |
|---|---|---|---|
| 5,313,542 A * | 5/1994 | Castonguay | 385/115 |
| 5,587,832 A * | 12/1996 | Krause | 359/385 |
| 5,861,910 A | 1/1999 | McGarry | |
| 5,923,466 A * | 7/1999 | Krause et al. | 359/389 |
| 6,038,067 A * | 3/2000 | George | 359/368 |
| 6,286,969 B1 | 9/2001 | Kurokawa | |
| 7,072,034 B2 * | 7/2006 | Rosengaus et al. | 356/237.5 |

FOREIGN PATENT DOCUMENTS

| | | |
|---|---|---|
| DE | 37 34 691 A1 | 4/1988 |
| EP | 1 024 355 A | 8/2000 |
| WO | WO 85/04014 A | 9/1985 |
| WO | WO 99/22262 A | 5/1999 |
| WO | WO 99/63327 A | 12/1999 |
| WO | WO 01/69210 A | 9/2001 |

* cited by examiner

DARK FIELD IMAGING DEVICE FOR THE SPATIALLY-RESOLVED DARK FIELD IMAGING OF A SAMPLE AND EXAMINATION METHOD

FIELD OF THE INVENTION

The present invention relates to the field of fluorescence images in which, following absorption of an excitation radiation, the fluorescence radiation of a sample is utilized to analyze the properties of the sample, and relates especially to a dark-field imaging device for the spatially resolved dark-field imaging of a sample.

BACKGROUND OF THE INVENTION

In fluorescence imaging, a light source having a broad spectral density distribution, such as a xenon or mercury arc lamp, ensures that many different fluorescent materials can be utilized. Through an exciter filter, the sample is illuminated with only that portion of the spectrum to which the fluorescent dye is sensitive. At the same time, a darker background is achieved, and organic samples that, for example, are destroyed or altered by UV light are protected. An additional barrier filter in the optical path of the fluorescent light ensures enhanced contrast.

One of the advantages of fluorescence microscopy, in which the wavelengths of the excitation light and the detected light are different, over transmission or reflection microscopy, which work with identical wavelengths, lies in the characteristic properties of fluorescent light since, in addition to the radiation intensity, important information about the sample can also be gathered from the fluorescence lifetime, the spectral distribution and the polarization.

In a conventional reflected-light fluorescence microscope, the sample is irradiated with light, and fluorescent dyes with which the sample was stained emit the fluorescent light that the experimenter can observe through the eyepiece. With the aid of a filter, the excitation light that is also still entering the detection optical path is suppressed so that the fluorescence is not outshone.

The reflected-light fluorescence microscope further includes a dichroic splitter mirror, whose task is to reflect the excitation radiation to the sample as completely as possible, and to transmit the fluorescent light to the eyepiece as completely as possible. Thus, its dichroism is selected such that the mirror is transparent for the fluorescence wavelength, and is a mirror for the excitation wavelength. Depending on the optical path, a reverse distribution of transparency and mirroring can also be realized; the splitter mirror then constitutes a mirror for the fluorescence wavelength and is transparent for the excitation wavelength. In both cases, the exciter filter, the dichroic splitter mirror and the barrier filter form a component part that is simply interchanged by swiveling.

In transmitted-light fluorescence microscopes, the requirements for the filter are very high, and it is hardly possible to achieve a dark background.

Dark-field microscopes do not allow any direct microscope light to enter the objective. Here, the sample is not illuminated with a cone of light, but rather only with the envelope of a cone. This cone envelope is prepared by a special condenser, known as a dark-field condenser. If there is no sample in the optical path, the field of view remains completely dark when looking into the eyepiece. If, on the other hand, a specimen is placed in the optical path, the microscope light is partially deflected by the sample structures through refraction, reflection, diffraction or scattering. Some of the light deflected in this way now enters the objective and produces a visible image in the microscope. The objects thus generally appear brightly glowing on a dark background. Here, particularly the edges and scattering interfaces glow; the interior of an object usually remains dark.

In laser scanning microscopes, the sample is analyzed in a scanning method with the aid of a laser beam that scans the sample. The grid-point data measured is subsequently composed into an image of the sample.

The advantage of confocal light microscopy consists in the possibility to collect the light reflected or emitted by the sample from a single depth plane. A pinhole aperture that is conjugate to the focal plane, or in other words, is disposed confocally, ensures that nearly all light that does not originate from the focal plane is not detected by the detector.

In a confocal laser scanning microscope, as with a laser scanning microscope, an image is composed point by point and line by line from a sequential scanning. By shifting the focal plane, the two-dimensional images of a specific depth, the optical cuts, can be composed into a three-dimensional image, and in particular, can be further processed digitally.

However, each of the methods cited exhibits disadvantages. For example, in fluorescence imaging, the required suppression of the excitation light by filters limits the signal-to-noise ratio that can be achieved.

Excitation with a laser scanner offers the benefit of narrow spectral width of the excitation light; however, the collinear optical paths also make good filters necessary. In addition, the lasers utilized are costly and the scanning device requires intensive maintenance and repairs due to the movable parts.

If a CCD element is utilized as the detector, dark-field excitation is usually preferred. Then the signal-to-noise ratio is determined by the inherent noise of the CCD chip, so that in order to achieve higher sensitivities, long integration times are needed and the element must be cooled utilizing a Peltier cooler or liquid nitrogen. This solution is costly, too, due to the utilization of technically sophisticated CCD elements, and their high resolution is not needed and not used for many applications.

DESCRIPTION OF THE INVENTION

This is where the present invention begins. The object of the present invention, as characterized in the claims, is to create an imaging device for the spatially resolved imaging of a sample, especially a fluorescent sample, that avoids the disadvantages of the background art. In particular, an imaging device shall be provided that exhibits high sensitivity with a simple, robust and low-priced design. In the present context, an average spatial resolution of the imaging device from typically about 10 to about 1000 imaging points is sufficient.

According to the present invention, this object is solved by the dark-field imaging device according to claim 1. Further embodiments of the invention are evident from the dependent claims 2 through 11. The present invention also provides, for the examination of a sample having a plurality of test sites, utilizing such a dark-field imaging device, a method according to claim 12. Preferred features of the method are the subject of the dependent claims 13 through 16.

According to the present invention, the dark-field imaging device for the spatially resolved dark-field imaging of a sample, especially a fluorescent sample, comprises an illumination assembly for the illumination of the sample with excitation light, comprising a grid of individually addressable light sources, wherein the lines connecting the light sources and the sample define a region with the optical path of the direct excitation light and a region with the optical path of the specular reflected excitation light. The illumination assembly is arranged and adapted such that the light cones of the individual light sources each illuminate substantially non-overlapping regions of the sample. The imaging device further comprises a detection assembly for detecting the radiation emitted by the sample as an optical response to the illumination having radiation-receiving elements, wherein the radiation-receiving elements of the detection assembly are disposed outside the region with the optical path of the direct excitation light and the region with the optical path of the specular reflected excitation light.

Thus, the present invention is based on the idea of utilizing the principle of dark-field illumination in a spatially resolved imaging device to enhance contrast and to achieve the spatial resolution not through the detection portion of the device, but rather through spatially resolved excitation of the sample. On the one hand, this allows expensive components such as excitation lasers or cooled CCD elements to be dispensed with and, on the other hand, it allows high detection sensitivity through the utilization of highly sensitive single detectors.

In a preferred embodiment, the detection assembly exhibits as radiation-receiving elements a plurality of light guides, each of whose one end receives the radiation emitted by the sample outside the region with the optical path of the direct excitation light and the optical path of the specular reflected excitation light, and whose other end is connected to a common single detector.

Here, multiple groups of light guides can also be provided, each of which may be jointly connected to a single detector. Since the number of light guides than can be jointly connected to a single detector is limited due to the finite size of the light guides, it may be necessary, when disposing a large number of light guides, to provide multiple single detectors, each of which covers, for example, different ring-shaped solid-angle regions $\Delta\theta$.

The one ends of the plurality of light guides are here advantageously disposed radially-symmetrically with respect to a common central axis. This allows a high detection yield and, simultaneously, high detection homogeneity across the surface of the sample.

Expediently, the single detector is a highly sensitive detector, especially a photomultiplier.

In a preferred embodiment of the present invention, the light-source grid forms an n×m matrix, where n lies between 2 and 100, and m between 1 and 100. For m=1, the light-source grid forms a light-source line of length n.

Here, expediently, the spacing between adjacent light sources is constant. However, variable spacing and other grid sizes also lie within the scope of the present invention.

Advantageously, the light sources are selected from the group comprising light-emitting diodes, laser diodes, an LCD display element, a TFT LCD display element, a field emission display element, an electroluminescent display element, a plasma display, a polymer display element, an illuminated spatial light modulator (SLM), especially a micromechanical digital mirror device (DMD), a vacuum fluorescent display (VFD) and a video projector.

Light-emitting diodes are particularly preferred as light sources since, in addition to having good radiation quality and sufficient output, they are economical, easy to address, and can be obtained for numerous wavelengths.

The light-source grid may also include light sources having different emission wavelengths. For example, each light source may illuminate, on the sample, multiple test sites that are marked with differing fluorescent dyes. An unambiguous linking of the optical response is then nonetheless possible by utilizing the different emission wavelengths of the light sources.

In an expedient embodiment, the illumination assembly includes, for imaging the light-source grid onto the sample of interest, an optical imaging assembly, especially an imaging lens. For imaging, however, all other per se known optical imaging assemblies are also conceivable. The sample may also be directly illuminated, for instance if the aperture angle of the illumination is limited by the aperture or by initial properties.

The detection assembly may be adjusted for the detection of an optical response radiation of the same wavelength as that of the excitation light, for instance in order to detect the scattered light produced in the sample. However, it is preferred that the detection assembly be adjusted for the detection of an optical response radiation that differs from the spectrum of the excitation light, especially for fluorescence emission of the sample.

An element for limiting the spectral width of the excitation light may be disposed between the light-source grid and the sample, especially a filter, a grating, an acustooptic modulator or a prism. If the excitation light source is sufficiently spectrally narrow, an element for spectral containment can also be dispensed with.

Likewise, the detection assembly may include an element for limiting the spectral width of the optical response radiation, especially a filter, a grating, an acustooptic modulator or a prism.

Moreover, a separation in time of excitation and detection may also be expedient. For example, a chopper wheel may open the optical path to the detector only after the excitation light has been switched off or blocked. However, this requires a sufficiently long lifetime of the excited fluorescence.

A method for the examination of a sample having a plurality of test sites with such a dark-field imaging device comprises the steps:

illuminating test sites by selectively addressing light sources of the light-source grid;

detecting the radiation emitted by the sample as an optical response; and evaluating the detected radiation for the relevant selectively addressed light sources.

Here, the light sources may be addressed serially, the detected radiation being linked to the illuminated test sites by linking the times at which the radiation was detected to the times at which the light sources were addressed.

Alternatively or additionally, at least a portion of the light sources may be addressed in a modulated manner, identically or differently, and the detected radiation is linked to the illuminated test sites by linking the modulation of the detected radiation to the addressing modulation of the light sources.

In addition, further possibilities for the linking of the detection signals to the relevant test sites are conceivable, such as taking into account the angle, position or radiation intensity. To the extent that another such linking possibility exists, overlapping illumination of the test sites can be permitted without losing the full mapability of signal and test site.

Preferably, to every test site of the sample is linked at least one light source of the light-source grid, which illuminates it with no further movement when the light source is addressed. Then the elaborate addressing required for scanning units of conventional photomultiplier devices, in which either the detector, the laser spot or the entire imaging optics must be shifted, is omitted.

However, it is also possible to provide a partial movement of the light-source grid, in other words, a combination of selective addressing of the light-source grid with a scanning movement, for example by scanning individual lines of the sample.

The method is particularly well suited for examining samples that do not have too many test sites, especially for samples having 5 to 2000 test sites, preferably having 50 to 500 test sites, particularly preferably from 100 to 200 test sites.

It will be appreciated that, in addition to the cited measures, further per se known methods for suppressing noise, for example a repeated measurement to improve the statistics, may be applied within the scope of the present invention.

Further advantageous embodiments, features and details of the invention are evident from the dependent claims, the description of the exemplary embodiment and the drawings.

BRIEF DESCRIPTION OF THE DRAWINGS

The present invention will be explained in further detail below by reference to exemplary embodiments in conjunction with the drawings. Only the elements that are essential to understanding the present invention are illustrated.

MANNER OF EXECUTING THE INVENTION

Figure 1:
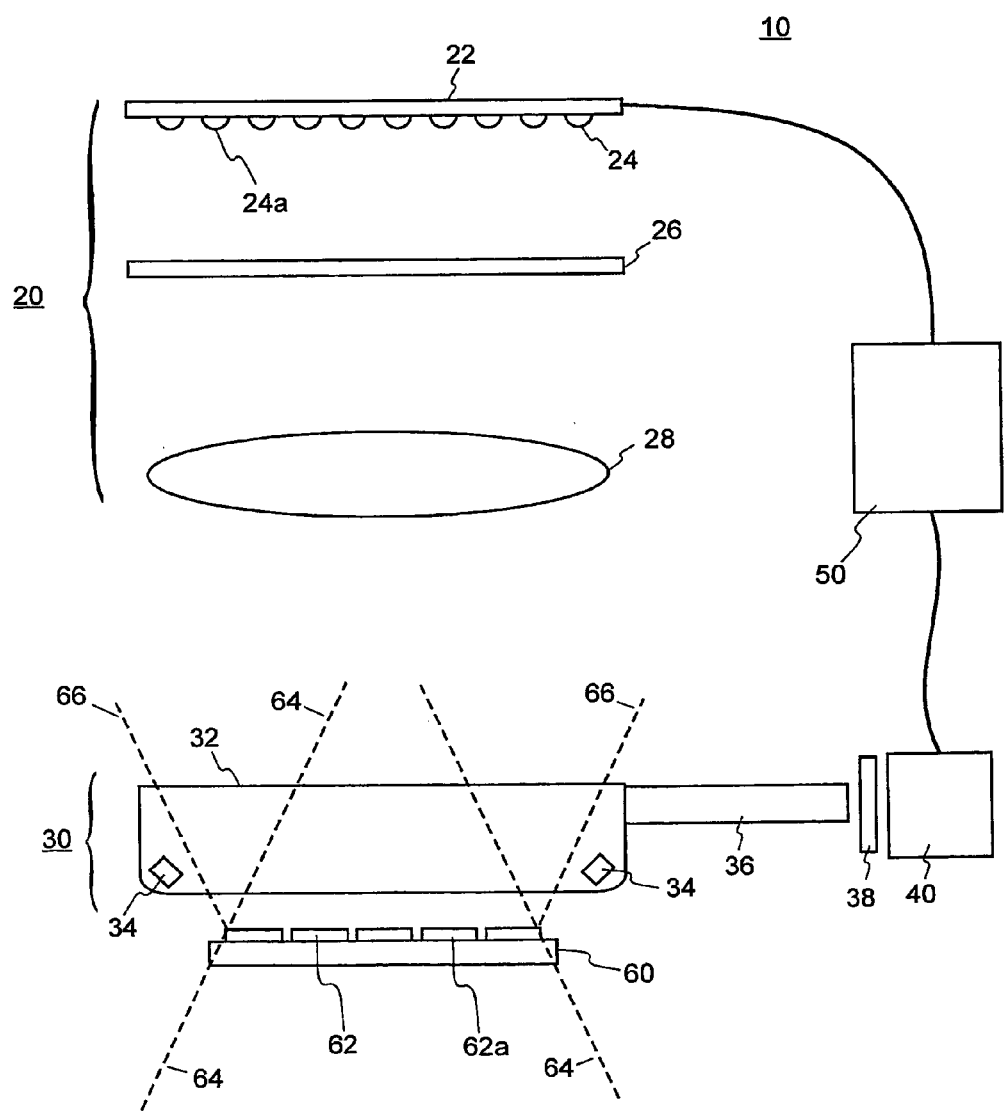
FIG. 1 Shows a schematic layout of a dark-field imaging device according to an exemplary embodiment of the present invention.
Figure 2:
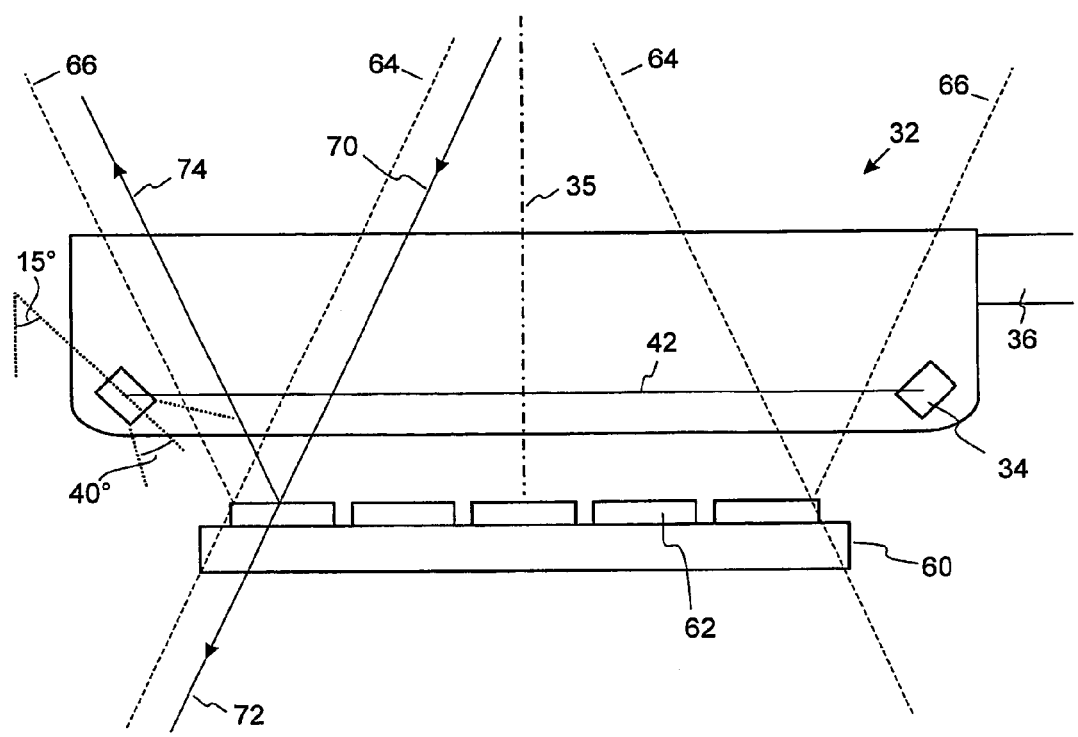
FIG. 2 Shows a more detailed layout of the detection assembly of the dark-field imaging device of FIG. 1.

With reference to the schematic layout of FIGS. 1 and 2, reference sign 10 designates a dark-field imaging device according to an exemplary embodiment of the invention. The dark-field imaging device 10 comprises an illumination assembly 20 having structured lighting, namely having a light-source grid 22 including 10×10 individually addressable light-emitting diodes 24. The light-emitting diodes are uniformly arranged in the LED grid 22 with spacing of 1 mm in both spatial directions, and are formed in the exemplary embodiment by InGaAlP LEDs having an emission wavelength of 645 nm.

The sample 60 of interest is disposed on a sample holder (not shown) in such a way that an image of the LED grid 22 is imaged onto the sample surface via the lens 28.

For limiting the spectral width of the excitation light, between the LED grid 22 and the lens 28 is inserted an interference filter 26 that transmits light only in a narrow wavelength range around 645 nm.

The optical response to the excitation, emitted by the sample 60, which in the exemplary embodiment is substantially given by fluorescence radiation at 680 nm, as described in detail below, is detected by a detection assembly 30. The detection assembly 30 comprises a ring detector 32, which is described in greater detail below, a photomultiplier 40, and, disposed in front of the photomultiplier 40, a second interference filter 38 that transmits light only in a narrow wavelength range around 680 nm.

The photomultiplier 40 and the LED grid 22 are connected to a control and evaluation unit 50 that addresses the LED grid 22 and detects the light intensity detected by the photomultiplier 40 and evaluates it based on the addressing data.

The ring detector 32 includes a plurality of light guides, the end pieces 34 of which are disposed radially-symmetrically around a central axis 35 (FIG. 2) of the ring detector in a plane 42 parallel to the surface of the sample 60 and with their openings directed to the sample 60. As illustrated in FIG. 2, in the exemplary embodiment, the end pieces 34 point to the sample at an angle of 1520 to the vertical with an aperture angle of 40°. The light guides are led jointly in a tube 36 to the photomultiplier 40.

With respect to the sample 60, the ring detector 32 is dimensioned and disposed such that a dark-field image of the sample 60 is obtained.

With reference to FIG. 2, the geometric optical path of the light beams of the direct excitation light 70 and 72 defines a region 64 with the optical path of the direct excitation light. All direct excitation radiation is localized within this truncated cone of radiation 64 emanating from the LED grid 22.

In the same way, the geometric optical path of the specular reflected (angle of incidence=angle of reflection) light beams 74 of the excitation light defines a region 66 with the optical path of the specular reflected excitation light. All specular reflected excitation radiation is localized within this truncated cone of radiation 66 emanating from the sample 60.

The ring detector 32 is now disposed such that all of the light guide ends 34 lie outside the regions 64, 66. Thus, no direct or specular reflected excitation light enters a radiation-receiving element. A fluorescence emission of the sample 60, on the other hand, is radiated non-directionally into a solid angle of $4\pi$, and so also reaches the light guide ends 34 of the detector.

The ring shaped arrangement of the light guide ends 34 allows a high detection yield and, simultaneously, high detection homogeneity across the surface of the sample 60.

In order to obtain a particularly homogeneous detection of the optical sample response, the vertical position 42 of the light guide ends 34 of the ring detector can be adjusted as follows: First, to the tube 36 is connected, in place of the photomultiplier 40, a light source that feeds, for instance, white light into the light guides. The light guide ends 34 then function as a ring light source. The height of the ring detector 32 is now adjusted such that the surface of the sample is illuminated as homogeneously as possible. This can be judged visually or by a measurement at the sample location, for example with a CCD chip. Then the light source at the tube end is again exchanged for the photomultiplier 40. The vertical position of the ring detector 32 is now also optimally adjusted for a homogeneous detection of the sample emission. A calibration of the measuring points can occur subsequently by measuring the scattered light of a scattering surface.

In the exemplary embodiment, the sample 60 is itself structured, and includes an array of 10×10 test sites 62, of which only a few are shown schematically in the diagram in FIG. 1.

In the exemplary embodiment, the sample 60 is especially a biosensor chip made of a two-dimensional array of test sites 62, in which every test site exhibits specific probe molecules. Here, the probe molecules are fixed on a surface and can specifically react with chemical substances from an analysis substance. Through the attachment of fluorophores, excitable in the exemplary embodiment at 645 nm and emitting at 680 nm, it is achieved that the occurrence or non-occurrence of a reaction at a test site can be detected via the appearance or non-appearance of a fluorescence emission at the location of the test site.

In the exemplary embodiment, the illumination system 20 and the sample 60 are adjusted to each other in such a way that every test site 62 can be illuminated by exactly one LED 24. If, for example, at a specific point in time, only the LED 24a is addressed by the control and evaluation unit 50, while the remaining LEDs remain dark, only the corresponding test site 62a will be illuminated. In the same way, the other test sites can be selectively illuminated.

If the correspondence of test sites 62 and LEDs 24 has been defined, the control and evaluation unit 50 can then link the fluorescent light integrally detected by the detection assembly 30 to the test site 62a. By sequentially addressing all LEDs 24 and sequentially detecting the fluorescent light, the sample response can be detected spatially resolved, without requiring a spatially resolving detector.

The linking of the detection signal to a test site 62 can also occur in another way, that is, by sequentially addressing the LEDs 24. For example, a first LED can be addressed in a modulated manner with a first frequency, for example 40 Hz, and a second LED with a second frequency, for example 70 Hz. The response signals of the corresponding test sites are then likewise modulated with 40 Hz or 70 Hz, and can thus be separated and linked in the control and evaluation unit 50.

The invention claimed is:

1. A dark-field imaging device for the spatially resolved dark-field imaging of a sample (60), comprising
    an illumination assembly (20) for the illumination of the sample with incident light, wherein the excitation light conically impinges on the sample and is partially specular reflected thereby, thus defining a region (64) with the optical path of the direct excitation light, and a region (66) with the optical path of the directionally reflected excitation light, wherein the illumination assembly (20) comprises a grid (22) of individually addressable light sources (24), which are arranged and adapted such that the light cones of the individual light sources (24) each illuminate substantially non-overlapping regions of the sample, and
    a detection assembly (30) having a plurality of light guides whose one ends (34) receive the radiation emitted by the sample outside the region (64) with the optical path of the direct excitation light and the region (66) with the optical path of the directionally reflected excitation light, and whose other ends are connected to a common single detector (40),
wherein the light sources (24) are serially addressable for the spatially resolved excitation of the sample and for the linking of the times at which the optical radiation was detected to the times the light sources (24) were addressed.

2. The dark-field imaging device according to claim 1, in which the one ends (34) of the plurality of light guides are disposed radially-symmetrically with respect to a common central axis (35).

3. The dark-field imaging device according to claim 1 or 2, in which the single detector is a photomultiplier (40).

4. The dark-field imaging device of claim 1, wherein the light-source grid (22) forms an n×m matrix, wherein n lies between 2 and 100, and m between 1 and 100.

5. The dark-field imaging device of claim 1, wherein the light sources (24) are selected from the group comprising light-emitting diodes, laser diodes, an LCD display element, a TFT LCD display element, a field emission display element, an electroluminescent display element, a plasma display, a polymer display element, an illuminated spatial light modulator (SLM), a vacuum fluorescent display (VFD) and a video projector.

6. The dark-field imaging device of claim 1, wherein the light-source grid (22) includes light sources (24) having different emission wavelengths.

7. The dark-field imaging device of claim 1, wherein the illumination assembly includes an optical imaging assembly (28) for imaging the light-source grid (22) onto the sample (60) of interest.

8. The dark-field imaging device of claim 1, wherein the detection assembly (30) is arranged for the detection of an optical response radiation that differs from the spectrum of the excitation light.

9. The dark-field imaging device according to claim 8, in which the illumination assembly (20) includes, disposed between the light-source grid (22) and the sample (60), an element (26) for limiting the spectral width of the excitation light.

10. The dark-field imaging device according to claim 8 or 9, in which the detection assembly (30) includes an element (38) for limiting the spectral width of the optical response radiation.

11. A method for the analysis of a sample having a plurality of test sites with a dark-field imaging device according to claim 1 having the steps:
    illuminating test sites by selectively addressing light sources of the light-source grid;
    detecting the radiation emitted by the sample as an optical response;
    evaluating the detected radiation for the relevant selectively addressed light sources; and
    linking the detected radiation to the illuminated test sites.

12. The method according to claim 11, in which the light sources are addressed serially, and the detected radiation is linked to the illuminated test sites by linking the times at which the radiation was detected to the times at which the light sources were addressed.

13. The method according to claim 11, in which at least a portion of the light sources is addressed in a modulated manner, and the detected radiation is linked to the illuminated test sites by linking the modulation of the detected radiation to the addressing modulation of the light sources.

14. The method of claim 11, wherein every test site of the sample is linked to at least one light source of the light-source grid, which illuminates it with no further movement when the light source is addressed.

15. The method of claim 11, wherein the plurality of test sites includes 5 to 1000 test sites.

16. The dark-field imaging device according to claim 1, wherein the sample (60) includes a fluorescent sample.

17. The dark-field imaging device according to claim 4, in which the spacing between adjacent light sources (24) is uniform.

18. The dark-field imaging device according to claim 7, wherein the optical imaging assembly (28) includes an imaging lens (28).

19. The dark-field imaging device according to claim 9, wherein the element (26) for limiting the spectral width of the excitation light includes one of a filter, a grating, an acustooptic modulator or a prism.

20. The dark-field imaging device according to claim 10, wherein the element (38) for limiting the spectral width of the optical response radiation includes one of a filter, a grating, an acustooptic modulator or a prism.

* * * * *